(12) United States Patent
Martin

(10) Patent No.: US 9,504,543 B1
(45) Date of Patent: Nov. 29, 2016

(54) ELECTRIC TOOTHBRUSH WITH CONTINUOUS ROTATING BRUSH AND VIBRATING SECTION

(71) Applicant: Paul Hammond Martin, Arcadia, FL (US)

(72) Inventor: Paul Hammond Martin, Arcadia, FL (US)

( * ) Notice: Subject to any disclaimer, the term of this patent is extended or adjusted under 35 U.S.C. 154(b) by 0 days.

(21) Appl. No.: 14/865,130

(22) Filed: Sep. 25, 2015

Related U.S. Application Data

(60) Provisional application No. 62/123,337, filed on Nov. 14, 2014, provisional application No. 62/179,388, filed on May 6, 2015.

(51) Int. Cl.
| | |
|---|---|
| *A46B 13/02* | (2006.01) |
| *A61C 17/26* | (2006.01) |
| *A61C 17/34* | (2006.01) |
| *A61C 17/24* | (2006.01) |

(52) U.S. Cl.
CPC ............ *A61C 17/349* (2013.01); *A46B 13/02* (2013.01); *A61C 17/24* (2013.01); *A61C 17/26* (2013.01); *A61C 17/3454* (2013.01)

(58) Field of Classification Search
CPC .. A46B 13/02; A46B 13/023; A61C 17/349; A61C 17/26; A61C 17/3454
See application file for complete search history.

(56) References Cited

U.S. PATENT DOCUMENTS

| | | | |
|---|---|---|---|
| 3,242,516 A * | 3/1966 | Cantor | A61C 17/26 15/28 |
| 5,170,525 A * | 12/1992 | Cafaro | A61C 17/22 15/180 |
| 5,177,826 A * | 1/1993 | Vrignaud | A61C 17/24 15/22.1 |
| 5,301,381 A * | 4/1994 | Klupt | A46B 11/06 15/22.1 |
| 5,416,942 A | 5/1995 | Baldacci et al. | |
| 5,864,911 A | 2/1999 | Arnoux et al. | |
| 6,178,579 B1 | 1/2001 | Blaustein et al. | |
| 6,189,693 B1 | 2/2001 | Blaustein et al. | |
| 6,647,577 B2 | 11/2003 | Tam | |
| 6,751,823 B2 | 6/2004 | Biro et al. | |
| 6,799,346 B2 * | 10/2004 | Jeng | A61C 17/349 15/22.1 |
| 7,024,718 B2 | 4/2006 | Chu | |
| 7,386,905 B2 | 6/2008 | Eliav et al. | |
| 8,281,443 B2 | 10/2012 | Brown et al. | |
| 8,584,292 B1 | 11/2013 | Djang | |
| 8,713,738 B2 | 5/2014 | Gatzemeyer et al. | |
| 8,813,300 B2 | 8/2014 | Woo et al. | |
| 2002/0020645 A1 | 2/2002 | Blaustein et al. | |

(Continued)

FOREIGN PATENT DOCUMENTS

| | | |
|---|---|---|
| CN | 201578391 U | 9/2010 |
| DE | 3406112 * | 8/1985 |

(Continued)

*Primary Examiner* — Randall Chin
(74) *Attorney, Agent, or Firm* — Hanrahan Law Firm, P.A.; Benjamin M. Hanrahan

(57) ABSTRACT

An electric toothbrush with perpetual rotating brush members and at least one vibrating, oscillating brush member is disclosed. The toothbrush includes a base, a brush head, and a main diving assembly disposed within the base and the brush head. The brush head includes a first rotating brush member and a second rotating brush member, the first rotating brush member being disposed in a first, continuous rotational direction, and the second rotating brush member being disposed in a second and opposite continuous rotational direction. An oscillating brush member is disposed between the rotating brush members and disposed in a side-to-side movement transverse to a longitudinal axis of the toothbrush.

13 Claims, 5 Drawing Sheets

(56) References Cited

U.S. PATENT DOCUMENTS

| | | |
|---|---|---|
| 2003/0084527 A1 | 5/2003 | Brown et al. |
| 2003/0140437 A1 | 7/2003 | Eliav et al. |
| 2003/0182744 A1 | 10/2003 | Fattori et al. |
| 2010/0330538 A1* | 12/2010 | Salazar .............. A46B 13/00 15/22.1 |
| 2012/0174938 A1 | 7/2012 | Hill |
| 2012/0279002 A1 | 11/2012 | Sokol et al. |
| 2013/0298340 A1 | 11/2013 | Suwanbutr |

FOREIGN PATENT DOCUMENTS

| | | | |
|---|---|---|---|
| DE | 102 29 148 | * | 1/2004 |
| EP | 1092399 A2 | | 4/2001 |
| WO | WO 2006/038058 | * | 4/2006 |

* cited by examiner

ELECTRIC TOOTHBRUSH WITH CONTINUOUS ROTATING BRUSH AND VIBRATING SECTION

CLAIM OF PRIORITY/CROSS REFERENCE TO RELATED APPLICATIONS

The present application is based on and a claim to priority is made under 35 U.S.C. §119(e) to the following U.S. provisional patent application Ser. No. 62/123,337, having a filing date of Nov. 14, 2014, and U.S. provisional patent application Ser. No. 62/179,388, having a filing date of May 6, 2015. The contents of both provisional patent applications are incorporated herein their entirety.

FIELD OF THE INVENTION

The present invention is generally directed to an electric or motorized toothbrush with a plurality of brush portions moving in a variety of different directions, and more specifically, an electric toothbrush with one or more, e.g., two, continuously rotating brush members and a side-to-side, oscillating or sonic brush member positioned there between.

BACKGROUND OF THE INVENTION

There are a number of motorized or electric toothbrushes that operate to drive or power the movement of one or more brushes disposed on or proximate an end of the toothbrush. However, many of the toothbrushes are exceptionally complex which can cause them to easily malfunction and/or otherwise not work in their intended manner. Furthermore, potentially due to design constraints, a number of electric toothbrushes fail to include a perpetual rotary brush that can function to rotate in a complete, non-oscillatory manner, and instead only include brush heads that oscillate.

There is thus a need in the art for an electric toothbrush with advance cleaning capabilities for advance oral hygiene. The proposed electric toothbrush may include one or more perpetual rotor or rotating brushes and one or more sonic or vibratory brushes, that when combined, provide an advanced and improved toothbrush for better cleaning and oral hygiene.

SUMMARY OF THE INVENTION

The present invention is generally directed to an electric toothbrush with at least one perpetual or continuous, non-oscillating brush member and at least one vibrating, sonic or oscillating brush member. In some embodiments, there are at least two perpetual or continuous brush members with at least one vibrating, sonic or oscillating brush member, for example, disposed between the rotating brush members. Further features of some embodiments may include opposite rotating brush members, such that a first rotating brush member may perpetually rotate (e.g., in a 360° manner) in one direction, while another rotating brush member of the same toothbrush perpetually rotates (e.g., in a 360° manner) in the opposite or other direction. Combined with the vibrating or oscillating brush member in between, the electric toothbrush of at least one embodiment will provide superior and advance cleaning or brushing capabilities. For example, while the perpetually or rotating brush(es) polish the teeth, the vibrating, sonic or oscillating brush member may be able to clean or brush deep within the teeth or between teeth, removing or brushing plaque or other matter that other brushes are unable to reach.

Various embodiments may be configured such that the head portion of the toothbrush is replaceable, for example, by disconnecting the head from a base portion of the body and replacing the head with a new or different one. The toothbrush may be powered by virtually any source of power, including, for example, via one or more replaceable or integrated DC batteries. An on/off or activation switch may be embedded within an easy grip or contoured handle for selectively activating and deactivating an electric drive motor.

These and other objects, features and advantages of the present invention will become more apparent when the drawings as well as the detailed description are taken into consideration.

BRIEF DESCRIPTION OF THE DRAWINGS

Like reference numerals refer to like parts throughout the several views of the drawings provided herein.

DETAILED DESCRIPTION OF THE INVENTION

Figure 1:
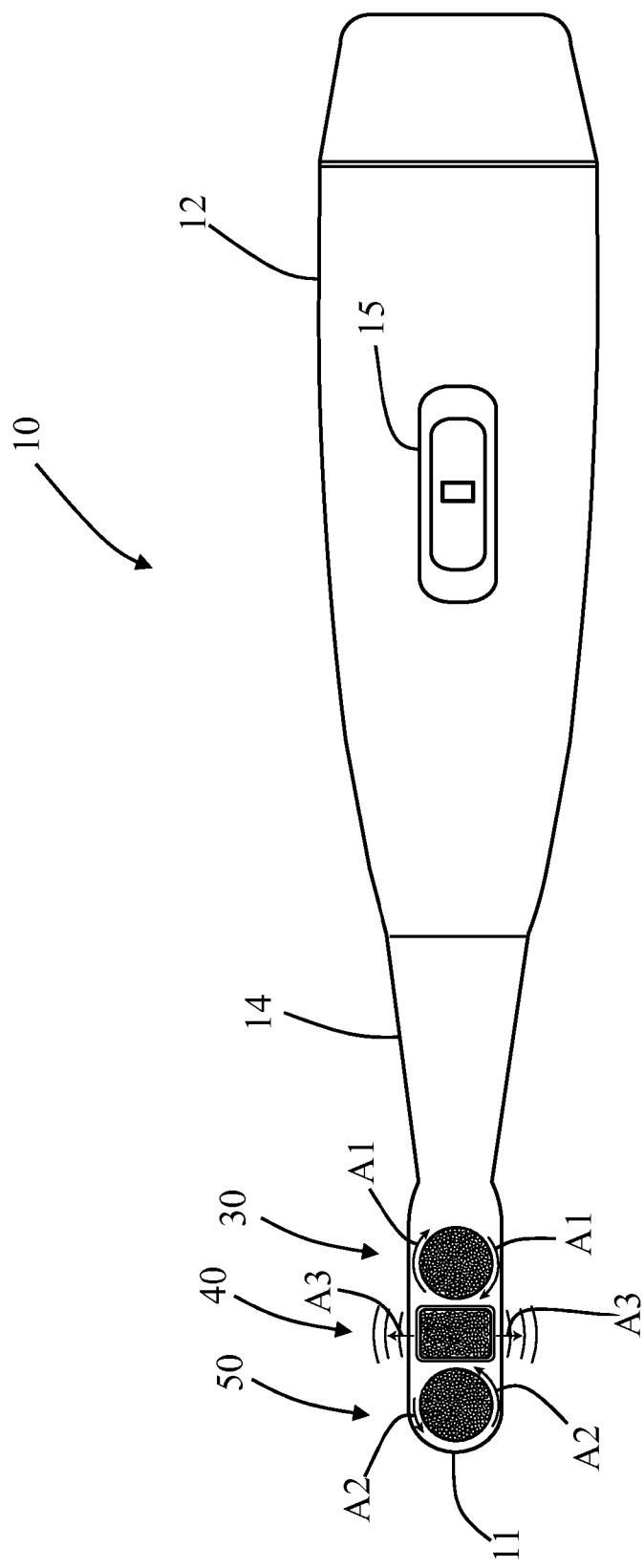
FIG. 1 is a top view of the toothbrush as disclosed in accordance with at least one embodiment of the present invention.

As shown in the accompanying drawings, and with particular reference to FIG. 1, the present invention is directed to an electric toothbrush, generally represented as 10. Specifically, the electric toothbrush 10 of the various embodiments includes an elongated body defined by a base 12 and a head 14. As will be described herein, certain embodiments include a main drive assembly 20 disposed on in the inside of the body, for example, inside the base 12 and/or head 14 portions, which, when activated, cause one or more brush members 30, 40, 50 disposed on the head 14 to move, e.g., rotate or oscillate. Accordingly, still referring to FIG. 1, an on/off or activation switch 15 may be disposed on the body and accessible to a user of the toothbrush 10. Manipulation of the switch 15, for example, by sliding, pushing, etc., will cause the main drive assembly 20 to activate and drive or movably dispose the brush members 30, 40, 50 in the intended manner.

Figure 2:
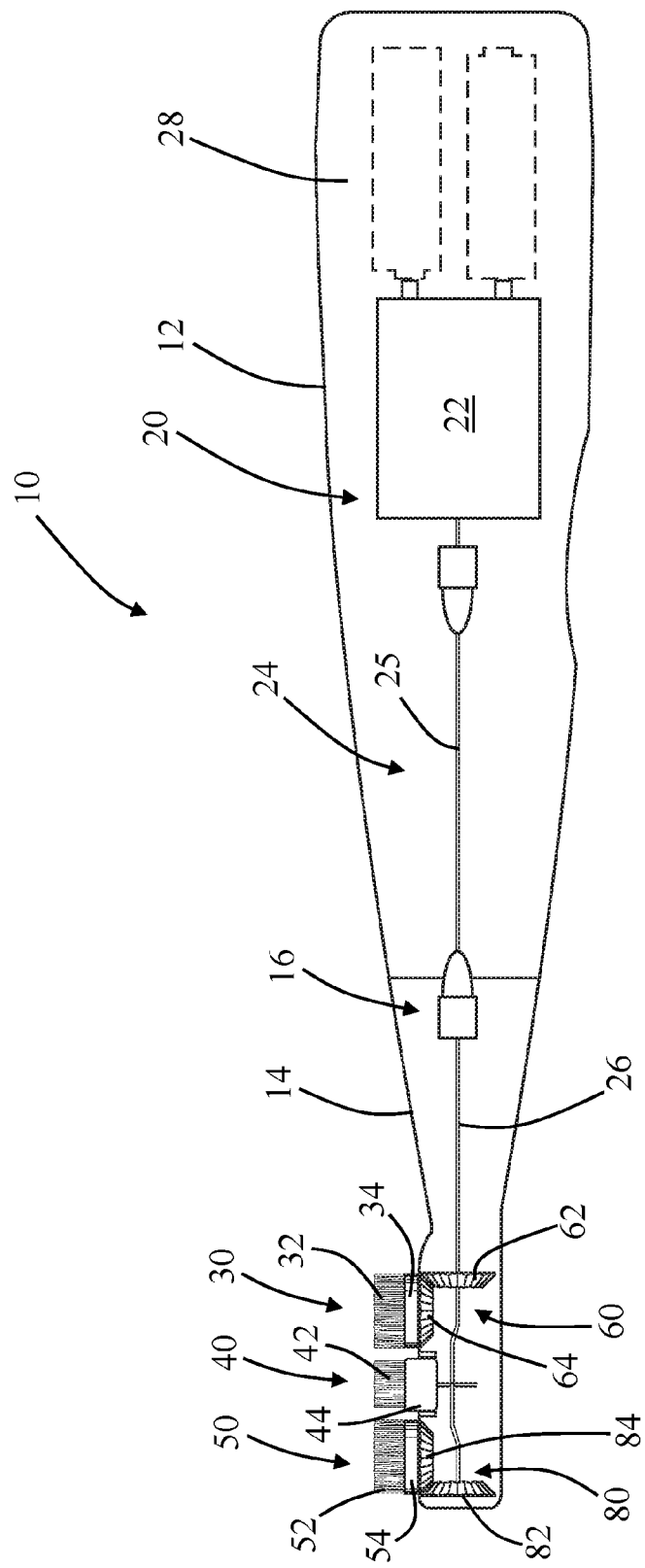
FIG. 2 is a side, partial sectional view of the toothbrush as disclosed in accordance with at least one embodiment of the present invention.

Referring to FIG. 2, the main drive assembly 20 of at least one embodiment may include an electric motor, generally represented as 22, a shaft assembly 24, and a power source 28. The power source 28 may include virtually any source of electric power supplied to the electric motor 22, including, for example, one or more batteries, as shown. The motor 22 is structured to drive the shaft assembly 24 in a manner such that the shaft assembly 24 is rotated along its longitudinal axis.

It should be noted that in certain embodiments, the head 14 may be removably interconnected to the base 12, for example, via a connection assembly 16, allowing the head 14, and therefore, the brush members 30, 40, 50 thereof, to be replaced, as needed or as desired. The connection assembly 16 may include virtually any cooperative attachment devices, including, snap attachment, one or more tabs, screws or threaded attachment ends, etc. Further, the shaft assembly 24 may include a first portion 25 embedded or otherwise substantially disposed within the base 12, and a second portion 26 embedded or otherwise substantially disposed within the head 14. The first and second portions 25, 26 of the shaft 24 may thus interconnect with one another, for example, via the connection assembly 16 or other attachment, such that when the drive assembly or motor 22 causes the first portion 25 of the shaft to rotate, the second portion 26 of the shaft 24 will also rotate. Thus, in at least one embodiment, rotation of the first portion 25 of the shaft 24 will be equal in speed and direction to rotation of the second portion 26 of the shaft 24.

Moreover, with reference to FIGS. 1 through 4, disposed at or near a distal end 11 of the head 14 is a plurality of brush members 30, 40, 50, and in particular, in at least one embodiment, a first rotating brush member 30, an intermediate oscillating brush member 40 and a second rotating brush member 50. Each of the brush members 30, 40, 50 of the various embodiments include a plurality of bristles 32, 42, 52, respectively, or other structures, surfaces or members, including nylon or other bristles, that are configured and generally known to be effective in cleaning or brushing the surface of a user's teeth or for other oral hygiene. The bristles 32, 42, 52 or other brushing structures may be fixedly attached to a corresponding brush base, for example, as shown at 34, 44, 54, respectively.

Figure 3:
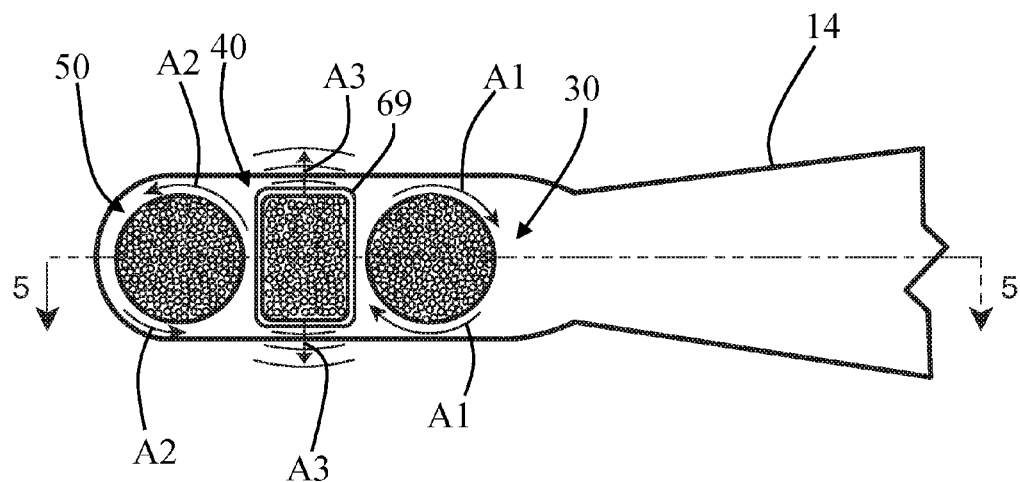
FIG. 3 is a top partial cut-away view of the head portion of the toothbrush as disclosed in accordance with at least one embodiment of the present invention.
Figure 4:
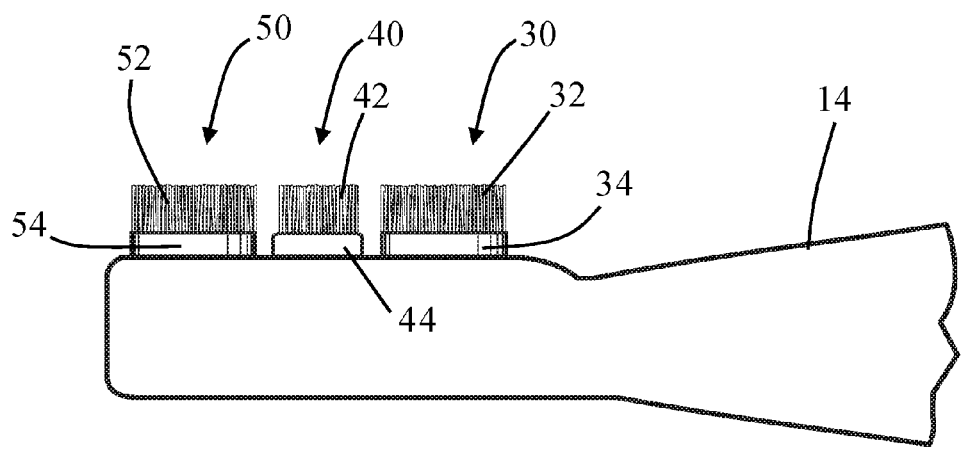
FIG. 4 is a side partial cut-away view of the head portion of the toothbrush as disclosed in accordance with at least one embodiment of the present invention.

Furthermore, as described herein, the first and second rotating brush members 30, 50 of at least one embodiment may spin or rotate in a continuous rotational movement about a corresponding axis generally or substantially perpendicular to the longitudinal axis of the elongated body or head 14. For example, as shown in FIGS. 1 and 3, the first rotating brush 30 of at least one embodiment will rotate or spin in a first continuous, non-oscillating rotational manner, meaning, in general, that the first brush member 30 may be configured to spin or rotate in a complete and continuous manner, for example, in three hundred and sixty degrees (360°), represented by arrows A1. Particularly, in at least one embodiment, the first brush member 30 will continuously or perpetually rotate in a first direction A1 and will not oscillate back-and-forth.

Similarly, still referring to FIGS. 1 and 3, the second rotating brush 50 of at least one embodiment will rotate or spin in a second continuous, non-oscillating rotational manner, meaning, in general, that the second brush member 50 may be configured to spin or rotate in a complete and continuous manner, for example, in three hundred and sixty degrees (360°), represented by arrows A2. Particularly, similar to the first brush member 30, in at least one embodiment, the second brush member 50 will continuously or perpetually rotate in a second direction A2 and will not oscillate back-and-forth.

For example, in at least one embodiment, the first and second rotating brush members 30, 50 may be configured to rotate in opposite directions, such that one of the brush members, e.g., the first brush member 30, will rotate in a clockwise direction when viewed from the position represented in FIGS. 1 and 3, and the second brush member 50 will rotate in an opposite counterclockwise direction when viewed from the same position. It should be noted, however, that in other embodiments, the first brush member 30 may operatively rotate in a counterclockwise manner, and the second brush member 50 may operatively rotate in a clockwise manner. The counter rotating brush members 30, 50 of at least one embodiment are capable of increasing the effective brushing and cleaning capacity of the toothbrush 10, as a whole. Further embodiments, however, may include first and second brush members 30, 50 rotating in the same, and common rotational direction, whether clockwise or counterclockwise.

Additionally, the first and second brush members 30, 50 of the various embodiments may comprise a generally round, oval or circular shape, as illustrated in FIGS. 1 and 3, for example, although other shapes and sizes may be contemplated within the full spirit and scope of the present invention.

Moreover, still referring to FIGS. 1 through 4, certain embodiments of the present invention further include an intermediate or additional brush member 40 configured to rapidly oscillate in a back-and-forth or side-to-side sonic movement, generally represented by arrows A3. For example, the oscillating brush member 40 of at least one embodiment may move in a direction generally or substantially transverse to a longitudinal axis of the toothbrush 10 or brush head 14, as shown in FIGS. 1 and 3. In certain embodiments, the oscillating brush member 40 is disposed between the first and second rotational brushes 30, 50, as shown in the drawings, although other placement on the brush head 14 may be contemplated. Also, as shown, the oscillating brush member 40 of at least one embodiment may include a general rectangular configuration, for example, with rounded corners, although other shapes and sizes are contemplated within the full spirit and scope of the present invention.

It should also be noted that the side-to-side, back-and-forth or sonic type of movement generated by the oscillating brush 40 of a least one embodiment, in combination with the continuous or perpetual rotational movement of the first and/or second brush members 30, 50 provide an enhanced and effective method of brushing and oral hygiene, in general.

Figure 5:
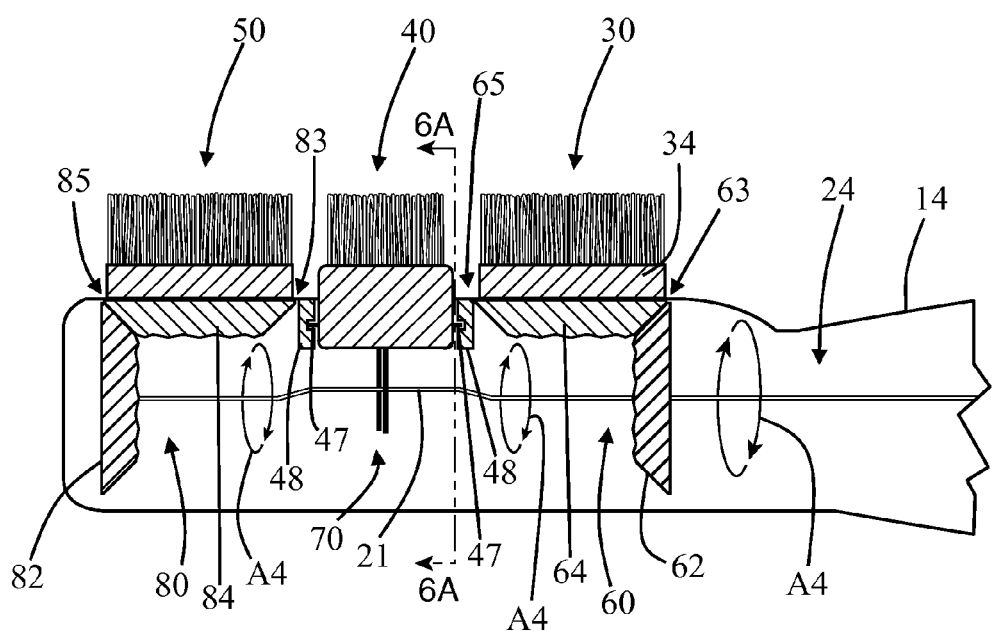
FIG. 5 is a section view along line 5-5 shown in FIG. 3.

With reference to FIGS. 2 and 5, certain embodiments further include brush driving assemblies, such as a first brush driving assembly 60 interconnected between the shaft 24 and the first rotating brush member 30, and a second brush driving assembly 80 interconnected between the shaft 24 and the second rotating brush member 50. Particularly, as the shaft 24 rotates, for example, as indicated by direction or rotational arrows A4, the brush driving assemblies 60, 80 are structured to correspondingly rotate or otherwise provide a rotational movement to the corresponding brush members 30, 50.

Specifically, in one illustrative embodiment, the brush assemblies 30, 50 each include a control portion, such as, but not limited to a control gear 62, 82 that is connected to the shaft 24 and rotates as the shaft 24 rotates. Particularly, in one embodiment, the control gears 62, 82 or other devices may be fixedly or otherwise connected to the shaft 24 such that as the shaft 24 rotates, for example, via directional arrows A4, the corresponding or connected control gears 62, 82 will also rotate in the same direction. In some cases, the shaft 24 is directly connected to the control gears 62, 82 such that the control gears 62, 82 will rotate at substantially the same speed as the shaft 24, although other intermediate connections, such as additional gears, reduction gears, or other devices may be implemented between the control gears 62, 82 and the shaft 24.

Furthermore, each of the brush assemblies 30, 50 of at least one embodiment also include a brush portion, such as, but not limited to a brush gear 64, 84, drivingly interconnected between the corresponding control gear 62, 82, respectively, and the corresponding brush member 30, 50, respectively. For example, in one embodiment, the first brush driving assembly 60 includes a control gear 62 connected to the rotating shaft 24, and a brush gear 64 interconnected between the control gear 62 and the first rotating brush member 30. For instance, the brush gear 64 may be connected to the base 34 of the first rotating brush member 30, either directly or indirectly, such that when the brush gear 64 is rotated, the corresponding base 34 and brush member 30 also rotates.

Specifically, in one embodiment, as the shaft 24 rotates, for example, in direction A4, the control gear 62 will also rotate, causing the brush gear 64 to rotate, causing the brush member 30 to rotate. As used herein the gears 62, 64 may include virtually any structure, device or part that imparts motion or movement from one structure to the other, and can, but does not necessarily, need to include corresponding teeth. Also, the gears 62, 64 may be of virtually any shape, size and ratio such that the rotational speed of one structure of gear may, but need not necessarily, equal the same speed of the interconnected structure or gear. As an example, the gears or other structures 62, 64 of at least one embodiment may include bevel gears, such that the rotational axes of the gears 62, 64 intersect one another, perhaps but not necessarily, perpendicularly.

In addition, the second brush driving assembly 80 may include a control gear 82 connected to the rotating shaft 24, and a brush gear 84 drivingly interconnected between the control gear 82 and the second rotating brush member 50. For instance, the brush gear 84 may be connected to the base 54 of the second rotating brush member 50, either directly or indirectly, such that when the brush gear 84 is rotated, the corresponding base 54 and brush member 50 also rotates.

Specifically, in one embodiment, as the shaft 24 rotates, for example, in direction A4, the control gear 82 of the second brush driving assembly 80 will also rotate, causing the brush gear 84 to rotate, causing the brush member 50 to rotate. As used herein the gears 82, 84 may include virtually any structure, device or part that imparts motion or movement from one structure to the other, and can, but does not necessarily, need to include corresponding teeth. Also, the gears 82, 84 may be of virtually any shape, size and ratio such that the rotational speed of one structure or gear may, but need not necessarily, equal the same speed of the interconnected structure or gear. As an example, the gears or other structures 82, 84 of at least one embodiment may include bevel gears, such that the rotational axes of the gears 82, 84 intersect one another, perhaps but not necessarily, perpendicularly.

Moreover, in certain embodiments, the control gears 62, 82 of at least one embodiment may be rotationally disposed in the same rotational direction, for example, in the same rotational direction as the shaft 24, as represented by arrows A4. Particularly, as described above, in one embodiment, the control gears 62, 82 are interconnected to the shaft 24, either directly or indirectly, such that the rotational movement of the shaft 24 is imparted to the control gears 62, 82. Thus, in such an embodiment, the control gears 62, 82 will function to rotate in the same direction, and at the same or different speed, as the shaft 24.

In some embodiments, however, as described above, the rotating brush members 30, 50 may rotate in opposite rotational directions. In order to impart rotational directions to the corresponding brush gears 64, 84 that are opposite to one another, in at least one embodiment, the control gears 62, 82 may be disposed on different ends of the corresponding brush gears 64, 84. For example, as shown in FIGS. 2 and 5, the first control gear 62 of the first brush driving assembly 60 is interconnected to a proximal end 63 of the corresponding brush gear 64. In the embodiment shown, the gears 62, 64 are illustrated as bevel gears although other structures configured to impart movement in the manner described are contemplated. Specifically, as the shaft rotates in direction of A4, the control gear 62 will also rotate in the direction of A4. Interconnection of the control gear 62 at the proximal end 63 of the brush gear 64 will cause the brush gear 64 (and thus the first rotational brush member 30) to rotate in a first rotational direction, such as a clockwise rotational direction as illustrated by arrows A1 in FIGS. 1 and 3.

Of course, if the shaft 24 is configured to rotate in a direction opposite to A4, the rotational directions of the control gear 62, brush gear 64 and first rotational brush member 30 will be opposite than that just described above. Furthermore, it is contemplated that the control gear 62 may be connected to a distal end 65 (e.g., an inner end) of the brush gear 64. In that case, with the shaft 24 and the control gear 62 rotating in direction A4, the brush gear 64 and the corresponding brush member 30 will rotate in a counterclockwise direction (not shown).

Referring again to FIG. 5, in at least one embodiment, the second control gear 82 of the second brush driving assembly 80 may be interconnected to a distal end 85 of the corresponding brush gear 84. In the embodiment shown, the gears 82, 84 are illustrated as bevel gears although other structures configured to impart movement in the manner described are contemplated. Specifically, as the shaft 24 rotates in direction of A4, the control gear 82 will also rotate in the direction of A4. Interconnection of the control gear 82 at the distal end 85 of the brush gear 84 will cause the brush gear 84 (and thus the second rotational brush member 50) to rotate in a second rotational direction, such as a counterclockwise rotational direction as illustrated by arrows A2 in FIGS. 1 and 3.

Also, if the shaft 24 is configured to rotate in a direction opposite to A4, which is contemplated, the rotational directions of the control gear 82, brush gear 84 and second rotational brush member 50 will be opposite than that just described above. Furthermore, it is contemplated that the control gear 82 may be connected to a proximal end 83 (e.g., an inner end) of the brush gear 84. In that case, with the shaft 24 and the control gear 82 rotating in direction A4, the brush gear 84 and the corresponding brush member 50 will rotate in a clockwise direction (not shown).

For instance, in at least one embodiment, in order to impart opposite rotational directions to the first and second brush members 30, 50, the control gears 62, 82 may be disposed on opposite ends of the corresponding brush gears 64, 84. Specifically, if the first control gear 62 is disposed on a proximal end 63 of the first brush gear 64, then the second control gear 82 is disposed on a distal end 85 of the second brush gear 84. Similarly, if the first control gear 62 is disposed on a distal end 65 of the first brush gear 64, then the second control gear 82 is disposed on the proximal 83 end of the second brush gear 84. The terms distal and proximal are used as relative positioning terms to illustrate the opposite positioning of the gears of at least one embodiment and should not be deemed limiting.

As shown in FIG. 5, at least one embodiment further includes an oscillating drive assembly, generally referenced as 70, which is structured to cause the oscillating brush member 40 to move in the back-and-forth or side-to-side oscillating direction, as described. For instance, the oscillating drive assembly 70 of at least one embodiment includes at least two pins 72, 74 extending from the base 44 of the oscillating brush member 40, such that the pins 72, 74 are positioned on opposite sides of the shaft 24, or otherwise, the shaft 24 being disposed between the pins 72, 74. For instance, as shown in FIG. 5, the shaft 24 of at least one embodiment includes an offset portion 21 along the length of the shaft 24 such that the offset portion 21 aligns with or is disposed between the pins 72, 74. In this manner, the pins 72, 74 of at least one embodiment will be disposed on opposite sides of the offset portion 21 of the shaft 24.

When the shaft rotates, for example, in direction A4, the offset portion 21 of the shaft 24 will repeatedly and alternately engage the pins 72, 74. As the shaft 24, and in particular, the offset portion 21 thereof, engages the pins 72, 74, the attached brush member 40 will oscillate side-to-side in a repetitive and fast manner. As an example, the distance between the pins 72, 74 may be extremely small, and in the range of approximately 1/16th of an inch, although other distances, whether greater or smaller are contemplated. Thus, the offset portion 21 of the shaft are dimensioned in a manner to allow the shaft 24, and in particular, the offset portion 21 thereof, to completely rotate or spin within the area defined between the pins 72, 74, although the shaft 24 will engage the pins 72, 74 in order to oscillate the brush member 40.

Figure 6A:
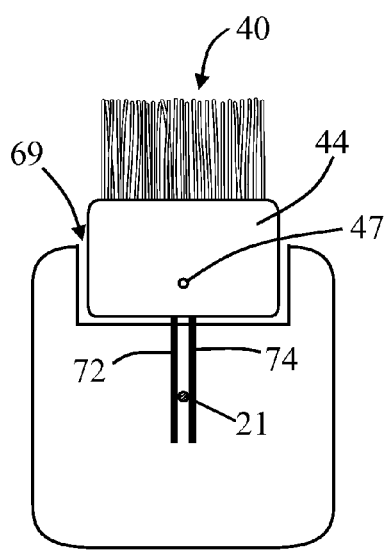
FIGS. 6A through 6C are partial sectional views along line 6A-6A shown in FIG. 5.
Figure 6C:
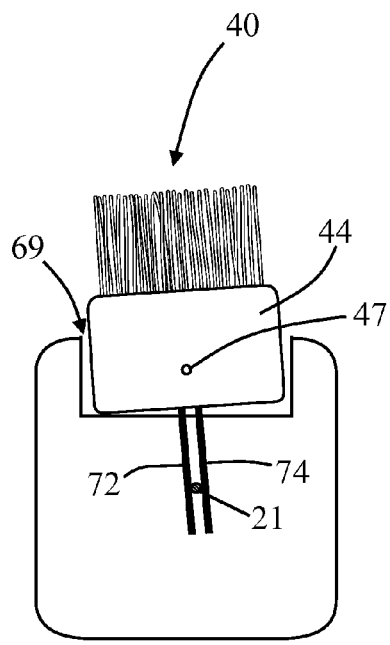
Figure 6B:
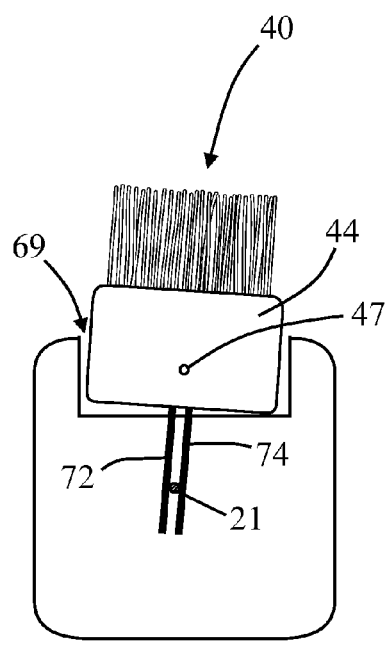

For example, FIGS. 6A through 6C illustrate an exemplary partial cut-away or sectional view of the oscillating brush member 40 of at least one embodiment. Particularly, for simplicity and to avoid confusion, the drawings in FIGS. 6A though 6C show the offset portion 21 of the shaft and its position within the area between the pins 72, 74. Specifically, in FIG. 6A, the brush member 40 is positioned in a relative middle or upright position as the offset portion 21 of the shaft is disposed between the pins 72, 74 and not engaging either. It should be noted that in FIGS. 6A, 6B and 6C, the offset portion 21 of the shaft of at least one embodiment may only engage, contact or push one of the pins 72, 74 at a time, for example, as the shaft or offset portion 21 thereof rotates and sweeps in a small circle, even though with the small clearance the drawings may appear to show it engaging both. In some embodiments, however, the offset portion 21 of the shaft 24 may be engaged by both pins 72, 74 at the same time, and as the offset portion 21 rotates or sweeps in a small circle, the pins 72, 74 will follow and oscillate the brush member, as described.

In particular, as the shaft rotates, for example, in a counterclockwise direction in FIGS. 6A through 6C, it will engage one of the pins 72, as shown in FIG. 6B, and knock the pins to the side, causing the corresponding brush member 40 to move. As the shaft continues to make a full 360° rotation, the offset portion 21 of the shaft will then engage the other pin 74, as shown in FIG. 6C, and knock the pins 72, 74 and, therefore the attached brush member 40 to the other side. As this shaft continues to rotate, and the offset portion 21 of the shaft continues to repetitively engage the pins 72, 74, the attached brush member 40 will oscillate back-and-forth or side-to-side in a repetitive and fast manner.

It should also be noted that, in the embodiment shown, when the offset portion 21 of the shaft engages one pin (e.g., (left) pin 72 in FIG. 6B), the brush member 40 will pivot or move in an opposite (e.g., right) direction. Similarly, in the same embedment, when the offset portion 21 of the shaft engages the other pin (e.g., (right) pin 74 in FIG. 6C), the brush member 40 will pivot or move in the other direction. However, in some implementations, for example, depending on where along the pins 72, 74, the shaft engages, it is possible that the brush member 40 may move or oscillate in the same direction as the engaged pin 72, 74. For example, when the shaft engages a left pin, the brush may move left, and when the shaft engages a right pin, the brush member will move right.

Furthermore, referring again to FIG. 5, the oscillating brush member 40 of at least one embodiment may include one or more stabilizing members, generally represented as 47, which correspondingly fit with a groove or channel disposed within a portion 48 of the housing or body of the toothbrush 10. For example, the stabilizing members 47 may extend off of the base 44 of the oscillating brush member 40 and fit within small grooves extending in the direction of the oscillating movement that allow the brush member 40 to move or oscillate. For instance, in the embodiment shown in FIG. 5, the oscillating brush member 40 will oscillate in a direction towards and away from the drawings (for instance, along the arrows A3 in FIG. 3). Thus, in this embodiment, the channels disposed within the portions 48 of the housing will extend toward and away from the drawing of FIG. 5, allowing the stabilizing members 47 to move therein as the oscillating brush member 40 oscillates.

Further, as shown in FIGS. 6A through 6C, the body or housing of the toothbrush may include a recess 69 within which the oscillating brush member 40 is disposed. The recess 69 of such an embodiment may be dimensioned to allow the oscillating brush member 40 to move back and forth or otherwise oscillate, as shown.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

Now that the invention has been described,

What is claimed is:

1. An electric toothbrush, comprising:
   a base, a brush head, and a main driving assembly disposed at least partially within said base,
   said brush head comprising a first rotating brush member operatively disposed in a single, continuous rotational direction such that said first rotating brush member does not rotationally oscillate in a back-and-forth manner,
   said brush head further comprising a second rotating brush member disposed in a single continuous rotational direction such that said second rotating brush member does not rotationally oscillate in a back-and-forth manner, and
   said brush head further comprising an oscillating brush member disposed between said first rotating brush member and said second rotating brush member, said oscillating brush member being disposed in a side-to-side only movement relative to said brush head, such that said oscillating brush member is not movable in a rotational manner relative to said brush head.

2. The electric toothbrush as recited in claim 1 wherein said single continuous rotational direction of said first rotating brush member is rotationally opposite than said single continuous rotational direction of said second rotating brush member.

3. The electric toothbrush as recited in claim 2 wherein said side-to-side movement of said oscillating brush member is transverse to a longitudinal axis of said brush head.

4. The electric toothbrush as recited in claim 3 further comprising a first brush driving assembly interconnected between a shaft and said first rotating brush member, and a second brush driving assembly interconnected between said shaft and a said second rotating brush member, said shaft being movable in a single, continuous rotational direction.

5. The electric toothbrush as recited in claim 4 wherein said first brush driving assembly comprises a control gear and a brush gear, said control gear being interconnected between said shaft and said brush gear, and said brush gear being drivingly connected to said first rotating brush member.

6. The electric toothbrush as recited in claim 5 wherein said second brush driving assembly comprises a control gear and a brush gear, said control gear of said second brush driving assembly being interconnected between said shaft and said brush gear of said second brush driving assembly, said brush gear of said second brush driving assembly being drivingly connected to said second rotating brush member.

7. The electric toothbrush as recited in claim 6 wherein said control gear of said first brush driving assembly and said control gear of said second brush driving assembly are disposed in a common rotational direction via said single, continuous rotational direction of said shaft.

8. The electric toothbrush as recited in claim 7 wherein said brush gear of said first brush driving assembly and said brush gear of said second brush driving assembly are disposed in opposite rotational directions.

9. The electric toothbrush as recited in claim 8 wherein said control gear of said first brush driving assembly is interconnected to a proximal end of said brush gear of said first brush driving assembly causing said first rotating brush member to rotate in a first, continuous rotational direction.

10. The electric toothbrush as recited in claim 9 wherein said control gear of said second brush driving assembly is interconnected to a distal end of said brush gear of said second brush driving assembly causing said second rotating brush member to rotate in a second, continuous rotational direction.

11. An electric toothbrush, comprising:

a base, a brush head, and a main driving assembly disposed at least partially within said base, said brush head comprising a first rotating brush member and a second rotating brush member, said first rotating brush member being disposed in a first, continuous rotational direction such that said first rotating brush member does not rotationally oscillate in a back-and-forth manner and wherein said first rotating brush member does not move in a side-to-side manner relative to said brush head, said second rotating brush member being disposed in a second continuous rotational direction such that said second rotating brush member does not rotationally oscillate in a back-and-forth manner and wherein said second rotating brush member does not move in a side-to-side manner relative to said brush head, said first, continuous rotational direction and said second, continuous rotational direction being rotationally opposite from one another, a first brush driving assembly drivingly connected to said first rotating brush member and a second brush driving assembly drivingly connected to said second rotating brush member, said first brush driving assembly and said second brush driving assembly being connected to a common shaft, said common shaft being movable in a single, continuous rotational direction, and an oscillating brush member disposed between said first rotating brush member and said second rotating brush member.

12. The electric toothbrush as recited in claim 11 wherein said oscillating brush member is disposed in a side-to-side directional movement transverse to a longitudinal axis of said brush head, wherein said oscillating brush member is not disposed in a rotational direction relative to said brush head.

13. The electric toothbrush as recited in claim 12 wherein said oscillating brush member comprises an oscillating drive assembly engaged by said common shaft for causing said oscillating brush member to be disposed in said side-to-side directional movement.

* * * * *